United States Patent
Uhrich

(10) Patent No.: US 6,365,146 B1
(45) Date of Patent: Apr. 2, 2002

(54) POLYMER ENCAPSULATION OF HYDROPHOBIC MATERIALS

(75) Inventor: Kathryn E. Uhrich, Hoboken, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/298,729

(22) Filed: Apr. 23, 1999

(51) Int. Cl.$^7$ ............... A61K 31/74; A61K 31/785; A61K 31/795; A61K 47/32; A61F 13/00

(52) U.S. Cl. ............... 424/78.31; 424/78.35; 424/78.37; 424/45; 424/451; 424/443; 424/464; 424/434; 424/449; 424/489; 514/772.4; 514/772.6

(58) Field of Search ............... 424/422, 425, 424/78.31, 78.35, 78.37, 45, 451, 464, 443, 434, 449, 489, DIG. 16; 514/772.4, 772.6

(56) References Cited

U.S. PATENT DOCUMENTS 5,830,986 A * 11/1998 Merrill ............ 528/425
6,007,845 A * 12/1999 Domb et al. ........ 424/501

OTHER PUBLICATIONS

ACS Symposium Series Apr. 1997 J.M.Harris et al pp. 218–225 91–115.*
Jansen et al., *JACS, 117*, 4417–4418 (1995).
Newkome et al., *Angew. Chem. Int. Ed. Engl., 30*, 1178–1180 (1991).
Liu et al., *Polym. Prepr., 38*(2), 582–583 (1997).
Jiang et al., *Polym. Mart. Sci. Eng., 78*, 194 (1998).
Uhrich, *Trends Polym. Sci., 5*(12), 388–393 (1997).
Roubi, "Hyperbranched Polymers Deliver Drugs Steadily," *C&EN, 77*, 63 (Jan. 18, 1999).
Jiang et al., "Novel Hyperbranched Polymeric Micelles as Controlled Drug Delivery Systems" (poster), 4th NJ Symp. Biomatter, Med. Dev. (Nov. 1997).
Liu et al., "Hyperbranched Polymers as a Controlled Release System,", 3rd NJ Symp. Biomater. Med Dev., (Nov. 1996).
Uhrich, "Hyperbranched Polymers for Drug Delivery Applications," *NIST Workshop on Properties and Applications of Dendritic Polymers* (Jul. 1998).
"Micellar Hyperbranched Polymers for Drug Delivery," *Contemporary Biomaterials Through Precise Control of Macromolecular Chemistry and Architecture* (ACS Polym. Div.–Sponsored Workshop, Nov. 1998).
Liu et al., *Polym. Prepr., 37*, 147–148 (1996).
Saketharaghavan et al., *Polym. Prepr., 38 (1)*, 628–629 (1997).
Liu et al., *Trans, Soc. Biomater., 20*, 363 (1997).
Liu, H., et al., "Hyperbranced polymeric micelles: drug encapsulation, release and polymer degradation", Department of Chemistry, Rutgers University, Piscataway, NJ, pp. 582–583.

* cited by examiner

Primary Examiner—Thurman K. Page
Assistant Examiner—S. Howard
(74) Attorney, Agent, or Firm—Schwegman, Lundberg, Woessner & Kluth, P.A.

(57) ABSTRACT

Polymers are provided having a structure selected from:

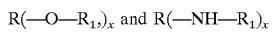

wherein R(—O—)$_x$ is a polyol moiety and R(—NH—)$_x$ is a polyamine moiety, with the x being between 2 and 10, inclusive, and each R$_1$ independently has the structure:

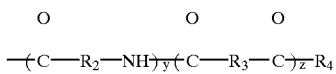

wherein

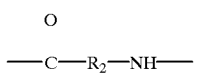

a divalent amino acid moiety with R$_2$ being a covalent bond or having from 1 to 8 carbon atoms, and y and z are between 0 and 10, inclusive, provided that y and z are not both 0;

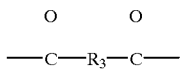

is a divalent dicarboxylic acid moiety in which R$_3$ is an alkylene or cyclolkylene group containing from 1 to about 15 carbon atoms substituted with a total of from 1 to about 10 hydroxyl groups, with at least a portion of the hydroxyl groups being acylated with 3 to 24 carbon atom carboxylic acids; and R$_4$ is a poly(alkylene oxide) having the structure:

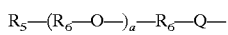

with R$_5$ selected from 1 to 40 carbon atom alkyl groups, —OH—, —OR$_7$, —NH—, —NHR$_7$, —NR$_7$R$_8$, —C—OH, —C—OR$_7$, —C—O—C—R$_7$, —C-NH$_2$, —C—NHR$_7$ and —C—NHR$_7$R$_8$; R$_6$, R$_7$ and R$_8$ are independently selected from 2 to 40 carbon atom, straight-chain or branched alkylene groups; Q is a divalent linkage moiety; and a is between 2 and 110, inclusive. Polymer encapsulates of hydrophobic molecules are also disclosed, including pharmaceutical dosage forms containing the encapsulates in which the hydrophobic molecule has biological or pharmaceutical activity, as well as transdermal delivery devices. Methods of treating patients with the pharmaceutical dosage forms are also disclosed.

21 Claims, No Drawings

POLYMER ENCAPSULATION OF HYDROPHOBIC MATERIALS

BACKGROUND OF THE INVENTION

The present invention relates to the encapsulation of hydrophobic molecules within polymeric micelles, and, in particular, to the encapsulation of materials such as biologically or pharmaceutically active hydrophobic molecules. The present invention further relates to pharmaceutical dosage forms comprised of thermodynamically stable aqueous solutions, suspensions or dispersions of the polymeric micelle encapsulated, biologically or pharmaceutically active, hydrophobic molecules. The present invention also relates to treatment methods employing the pharmaceutical dosage forms of the present invention.

SUMMARY OF THE INVENTION

The efficacy of pharmaceuticals is strongly affected by the way they are administered. There are many problems associated with the introduction of free drugs into the bloodstream. first, many drugs are deactivated when delivered in the free form. Although deactivation mechanisms can be quite complicated, interactions between drugs and components in the bloodstream (e.g., proteins and enzymes, as well as water) are the most common factors. Second, free drugs frequently have short circulation times (i.e., minutes) and are quickly excreted from the body. Third, free drugs are often distributed randomly among organs and tissues. The inability of most drugs to discriminate between normal and diseased cells contributes to drug toxicity, especially for anti-tumor drugs.

Another problem associated with drug delivery is water solubility; most drugs are too hydrophobic to be water-soluble. This water-insolubility limits both the applicable administration methods as well as dosage levels. Over the years, drug delivery system have been devised to overcome all or some of the problems described above, such as enhancing solubility and efficacy, prolonging circulation time, achieving controlled release, and providing site-specific delivery. Delivery systems range from the use of starch as an additive to form tablets, to the use of capsules to achieve slow release, to more complex devices consisting of hydrogels, polymers, liposomes and various surfactants.

The use of surfactants is one of the promising answers for drug delivery. The use of polymeric surfactants as drug delivery devices has been reviewed extensively, and several successful examples have been demonstrated. For example, micelles have a hydrophobic core that can solubilize hydrophobic materials, such as drugs, as well as a hydrophilic outer shell that makes the assembly water-soluble. Polymeric surfactants have been favored over smaller organic surfactants because they usually have much lower critical micelle concentrations, or cmc's (about $10^{-5}$ M), compared to smaller organic surfactants (about $10^{-2}$ M). Site-specific drug delivery has been shown possible by controlling the size or the surface properties of the polymeric surfactants. However, the thermodynamic instability that is both concentration and temperature dependent of these conventional micelles limits their use in drug delivery. The reversal of micelle to surfactant causes a flux of drug concentration which can cause serious toxicity problems.

One way to overcome the thermodynamic instability of conventional micelles is to construct an assembly that topologically resembles the micelle architecture but with all components covalently bound together. These assemblies are polymers consisting of both hydrophobic (usually aliphatic) and hydrophilic (ionic or non-ionic) components. Most examples of such materials are dendrimers with hydrophilic end functional groups based on amine or carboxylate groups. In a few systems, guest molecules have been entrapped within the structures. Jansen et al., *JACS*, 117, 4417–4418 (1995) demonstrated that different entrapped guest molecules could be liberated by selective chemical removal of the outer shell components. In general, unimolecular micelles showed either dynamic encapsulation (See, Newkome, et al., *Angew. Chem. Int. Ed. Engl.*, 30, 1178–1180 (1991)) or physical entrapment (Jansen et al.) of guest molecules depending on the steric compactness of the structures. The guest molecules either escape from the unimolecular micelles too soon (in the case of dynamic encapsulation) or do not diffuse at all (in the case of physical entrapment) unless the micellar structures are physically disrupted.

Liu et al., *Polym. Preprint.*, 38(2), 582–583 (1997) report the synthesis of hyper-branched polymeric micelles for encapsulation of small hydrophobic organic molecules. There remains a need for suitable delivery systems for the administration of hydrophobic drugs.

SUMMARY OF THE INVENTION

This need is met by the present invention. The present invention provides new polymeric micelles that are useful for solubilizing a variety of hydrophobic materials in water, particularly hydrophobic materials with biological or pharmaceutic activity, which greatly simplifies the preparation of aqueous dosage forms of biologically or pharmaceutically active hydrophobic materials.

Therefore, according to one aspect of the present invention, a polymer is provided having a structure selected from:

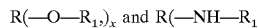

wherein $R(-O-)_x$ is a polyol moiety and $R(-NH-)_x$ is a polyamine moiety, with x being between 2 and 10, inclusive, and each $R_1$ independently has the structure:

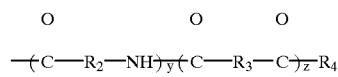

wherein

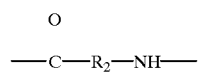

is a divalent amino acid moiety with $R_2$ being a covalent bond or having from 1 to 8 carbon atoms, and y and z are between 0 and 10, inclusive, provided that y and z are not both 0;

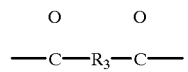

is a divalent dicarboxylic acid moiety in which $R_3$ is an alkylene or cycloalkylene group containing from 1 to about 15 carbon atoms substituted with a total of from 1 to about 10 hydroxyl groups, with at least a portion of the hydroxyl groups being acylated with 3 to 24 carbon atom carboxylic acids; and $R_4$ is a poly(alkylene oxide) having the structure:

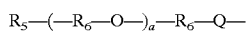

with $R_5$ selected from 1 to 40 carbon atom alkyl groups, —O—, $OR_7$—, —NH—, —$NHR_7$, $NR_7R_8$, —C—OH, —C—$OR_7$, —C—O—C—$R_7$, —C—$NH_2$, C—$NHR_7$, and —C—$NR_7R_8$; $R_6$, $R_7$ and $R_8$ are independently selected from 2 to 40 carbon atom, straight chain or branched alkylene groups; Q is a divalent linkage moiety; and a is between 2 and 110, inclusive;

provided that when y is zero and R is a 1,1,1-tris (hydroxyphenyl)ethane moiety, the divalent dicarboxylic moiety is not an acylated mucic acid moiety.

The polymers of the present invention encapsulate a wide variety of hydrophobic molecules. The encapsulation is a physical encapsulation, and not a simple association of the hydrophobic molecule with the polymer. According to a preferred embodiment of the present invention, upon formation of the encapsulated hydrophobic molecule, the polymer is recovered and rinsed to remove any residue of non-encapsulated hydrophobic molecules.

Therefore, according to another aspect of the present invention, a hydrophobic molecule encapsulated in a polymer is provided, wherein the polymer has a structure selected from:

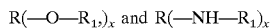

wherein $R(\!-\!O\!-\!)_x$ is a polyol moiety and $R(\!-\!NH\!-\!)_x$ is a polyamine moiety, with x being between 2 and 10, inclusive, and each $R_1$ independently has the structure:

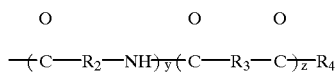

wherein

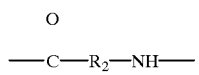

is a divalent amino acid moiety with $R_2$ being a covalent bond or having from 1 to 8 carbon atoms, and y and z are between 0 and 10, inclusive, provided that y and z are not both 0;

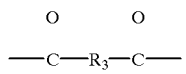

is a divalent dicarboxylic acid moiety in which $R_3$ is an alkylene or cycloalkylene group containing from 1 to about 15 carbon atoms substituted with a total of from 1 to about 10 hydroxyl groups, with at least a portion of the hydroxyl groups being acylated with 3 to 24 carbon atom carboxylic acids; and $R_4$ is a poly(alkylene oxide) having the structure:

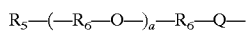

with $R_5$ selected from 1 to 40 carbon atom alkyl groups, —O—, —$OR_7$, —NH—, —$NHR_7$, —$NR_7$—$R_8$— C—OH, —C—$OR_7$, —C—O—C—$R_7$, —C—$NH_2$, —C—$NHR_7$ and —C—$NR_7R_8$; $R_6$, $R_7$ and $R_8$ are independently selected from 2 to 40 carbon atom, straight chain or branched alkylene groups; Q is a divalent linkage moiety; and a is between 2 and 110, inclusive;

provided that when y is zero and R is a 1,1,1-tris (hydroxyphenyl)ethane moiety, the divalent dicarboxylic acid moiety is not a mucic acid moiety acylated with carboxylic acids having less than six carbon atoms.

The present invention incorporates the discovery that acylation with carboxylic acids of six carbon atoms or greater produces an unexpected increase in the affinity of the polymer interior for hydrophobic molecules. The polymers of the present invention meet the need for unimolecular micellar encapsulants for hydrophobic molecules having biological or pharmaceutical activity that are thermodynamically stable in aqueous media. Accordingly, the hydrophobic molecules encapsulated by the polymers of the present invention are preferably hydrophobic molecules with biological or pharmaceutical activity.

Furthermore, because the polymer encapsulates of the present invention are thermodynamically stable in aqueous media, the present invention also includes aqueous solutions, suspensions and dispersions of polymer encapsulated hydrophobic molecules. Again, the hydrophobic molecules are preferably have biological or pharmaceutical activity.

The polymers of the present invention are ideal vehicles for the delivery of hydrophobic molecules with biological or pharmaceutical activity to patients in need thereof. Accordingly, the present invention also includes pharmaceutical dosage forms containing the polymers of the present invention encapsulating hydrophobic molecules having biological or pharmaceutical activity, and a pharmaceutically acceptable carrier. In addition, the present invention includes methods of treating a patient in need thereof with a hydrophobic molecule having biological or pharmaceutical activity by administering to the patient an effective amount of a pharmaceutical dosage form of the present invention.

While the pharmaceutical dosage forms may be aqueous solutions, suspensions or dispersions, other types of compositions are included among the dosage forms of the present invention, as well as among the dosage forms that are administered by the treatment methods of the present invention. The polymer encapsulated hydrophobic molecules may be administered in a solid form by way a of a tablet or capsule, for example, to be dissolved in the digestive tract, and, consequently, in the bloodstream.

Alternatively, pharmaceutical dosage form compositions may be prepared for topical administration. The present invention incorporates the discovery that the encapsulation of hydrophobic molecules by the polymers of the present invention enhances transdermal delivery of molecule. Absorption through the skin can be increased by a factor of up to 1000. Thus, the pharmaceutical dosage forms of present invention include dosage forms suitable for transdermal delivery, which, in addition to aqueous solutions, suspensions or dispersions, also include aqueous gels and water-in-oil and oil-in-water emulsions. The dosage form may be applied directly to the skin as a lotion, cream or salve, or a transdermal drug delivery device such as a transdernal patch may be employed, in which the polymer encapsulated hydrophobic molecule is retained in the active agent reservoir of the patch.

The polymer encapsulated hydrophobic molecules may be the only pharmaceutically or biologically active material in the topical dosage form, or the dosage form may contain the hydrophobic molecules stabilized in the pharmaceutical carrier by other means, so that the polymer encapsulated hydrophobic molecule provides a "burst effect" initial dose, followed by a sustained delivery of the non-encapsulated molecule.

Therefore, according to another aspect of the present application, a method for transdermal delivery to a patient in need thereof of a hydrophobic molecule having biological or pharmaceutical activity is provided. An effective amount of a topical dosage form containing the hydrophobic molecule encapsulated by the polymer of the present invention and a pharmaceutically acceptable topical carrier, is applied to the skin or mucosa of the patient.

Preferred polymers according the present invention hydrolyze into components known to be biocompatible, i.e., sugars, fatty acids, amino acids and poly(ethylene glycol). This also results in low cytotoxicity of the polymer and its hydrolysis products. The poly(alkylene oxide) units enhance the immunogenicity of the encapsulate, enabling the hydrophobic molecules to evade the body's immune system, thereby increasing the circulation time of the hydrophobic molecule. This allows for effective treatment with reduced quantities of the hydrophobic molecule, which, together with the enhanced immunogenicity, prevents or reduces the severity of incidents of toxic side effects.

The above and other objects, features and advantages of the present invention will become clear from the following description of the preferred embodiment.

DETAILED DESCRIPTION OF THE PREFERRED EMBODIMENT

The polymers of the present invention are prepared by coupling a plurality of hydrophobic moieties to the hydroxyl groups of a polyol core. The resulting polymer is then made water-soluble by attaching a poly(alkylene oxide) to the end of each hydrophobic moiety.

Polyols that are suitable for use as the polymer core are nearly limitless. Aliphatic polyols having from 1 to 10 carbon atoms and from 1 to 10 hydroxyl groups may be used, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, dulcitol, fucose, ribose, arabinose, xylose, lyxose, rhamnose, galactose, glucose, fructose, sorbose, mannose, pyranose, altrose, talose, tagitose, pyranosides, sucrose, lactose, maltose, and the like. More examples of aliphatic polyols include derivatives of glyceraldehyde, glucose, ribose, mannose, galactose, and related stereoisomers.

Aromatic polyols are preferred because of their hydrophobicity. Among the suitable aromatic polyols are 1,1,1-tris(4'-hydroxyphenyl)alkanes, such as 1,1,1-tris(4'-hydroxyphenyl) ethane, (1,3-adamantanediyl)diphenol, 2,6-bis(hydroxyalkyl)cresols, 2,2'-alkylene-bis(6-t-butyl-4-alkylphenols) 2,2'-alkylene-bis(t-butylphenols), catechol, alkylcatechols, pyrogallol, fluoroglycinol, 1,2,4-benzenetriol, resorcinol, alkylresorcinols, dialkylresorcinols, orcinol monohydrate, olivetol, hydroquinone, alkylhydroquinones, 1,1-bi-2-naphthol, phenyl hydroquinones, dihydroxynaphthalenes, 4,4'-(9-fluorenylidene)diphenol, anthrarobin, dithranol, bis (hydroxyphenyl) methane biphenols, dialkylstilbesterols, bis(hydroxyphenyl)alkanes, bisphenol-A and derivatives thereof, meso-hexesterol, nordihydroguaiaretic acid, calixarenes and derivatives thereof, tannic acid, and the like.

Other core polyols that may be used include cyclic crown ethers, cyclodextrines, dextrines and other carbohydrates such as starches and amylose. Alkyl groups may be straight-chained or branched, and may contain from 1 to 10 carbon atoms.

Hydrophobic moieties are coupled to two or more of the core polyol hydroxyl groups. Preferably, all of the hydroxyl groups of the core polyol are coupled to a hydrophobic moiety.

According to one embodiment of the present invention, the hydrophobic moiety is a dicarboxylic acid moiety containing from 1 to about 10 carbon atoms and substituted with from 1 to about 10 hydroxyl groups, wherein at least a portion of the hydroxyl groups are acylated with 3 to 24 carbon atom carboxylic acids. One carboxylic acid groups of the dicarboxylic acid is coupled to a hydroxyl group of the core polyol by way of an ester linkage, while the other carboxylic acid group remains free for coupling to the poly(alkylene oxide). The dicarboxylic acid may be a straight chained or branched, aliphatic or cycloaliphatic, dicarboxylic acid. Suitable aliphatic dicarboxylic acids include mucic acid, malic acid, citromalic acid, alkylmalic acid, hydroxy derivatives of glutaric acid, and alkyl glutaric acids, tartaric acid, citric acid, hydroxy derivatives of fumaric acid, and the like. Alkyl groups may be straight-chained or branched and may contain from 1 to 10 carbon atoms. The cycloaliphatic dicarboxylic acids include dicarboxylic acid derivatives of sugar alcohols.

The carboxylic acids acylating the hydroxyl groups of the dicarboxylic acids preferably contain from 6 to 24 carbon atoms. Preferably, every hydroxyl group of a dicarboxylic acid is acylated with a carboxylic acid.

The polyol coupled to two or more acylated dicarboxylic acid branches forms the hydrophobic core of the polymer of the present invention. According to another embodiment of the present invention, the volume of the cavity formed by the hydrophobic core of the polymer may be increased by inserting an amino acid or peptide linkage between the core polyol and each hydrophobic moiety. That is, a linkage as small as one amino acid up to the size of an oligopeptide containing 10 amino acid residues may be attached to each core polyol hydroxyl group or polyamine amino group, with the hydrophobic moiety being coupled to the end of the amino acid or peptide opposite the core polyol hydroxyl group or polyamine amino group.

The carboxylic acid terminus of an amino acid or peptide is coupled to a hydroxyl group of the core polyol by an ester linkage or an amino group of a core polyamine by an amide linkage. A carboxylic acid group of the acylated dicarboxylic acid is then coupled to the amine terminus of the amino acid or peptide by an amide linkage. The other carboxylic acid group again remains free for coupling to a poly (alkylene oxide). The number of amino acids employed in each peptide linkage should not be so great as to render the entire polymer water-insoluble. A peptide linkage containing from 3 to 6 amino acids is preferred. Preferred amino acids include lysine, serine, threine, cysteine, tyrosine, aspartic acid, glutamic acid and arginine. Like the other components of the polymers of the present invention, the amino acid linkages also hydrolyze to form biocompatible degradation products.

The free carboxylic acids on the end of each hydrophobic branch on the polyol core are then coupled to a poly (alkylene oxide). The poly(alkylene oxides) are preferably coupled to the free carboxylic acids by either ester or amide linkages. The alkylene oxide units contain from 2 to 4 carbon atoms and may be straight, chained or branched. Poly(ethylene glycol) (PEG) is preferred. Alkoxy-terminated poly(alkylene oxides) are preferred, with methoxy-terminated poly(alkylene oxides) being more preferred.

The poly(alkylene oxide) preferably has between about 2 and about 110 repeating units. A poly(alkylene oxide) having between about 50 and about 110 repeating units is more preferred.

The polymers of the present invention are prepared by first acylating the hydroxyl-substituted dicarboxylic acid. The dicarboxylic acid is reacted with a stoichiometric excess of the appropriate acyl chloride in the presence of a catalyst, if needed, such as $ZnCl_2$ with heating, up to about the reflux temperature of the reaction mixture. Those of ordinary skill in the art will understand that the appropriate acyl chloride will have from about 2 to about 24, and preferably from about 6 to about 24, carbon atoms.

The reaction continues until substantially complete, approximately 5 hours, after which the reaction product is extracted into an ether such as diethyl ether, followed by washing of the ether fraction with water, drying and evaporation. The resulting crude product is the purified by recrystallization.

The acylated dicarboxylic acid is then coupled to a core polyol by means of a carbodiimide-mediated coupling reaction. The core polyol and a stoichiometric excess of the acylated dicarboxylic acid are dissolved in a common solvent, such as an ether, for example, ethyl ether. Carbodiimide-mediated coupling reactions are disclosed in Bodanszky, *Practice of Peptide Synthesis*, (Springer-Verlag, New York, 1984) at page 145. A quantity of a solution providing a molar equivalent of a carbodiimide and N,M-dimethylaminopyridine (DMAP) for each polyol hydroxyl group, dissolved in a common solvent such as methylene chloride, is added to the reaction mixture. The reaction proceeds rapidly to completion, after which the urea side-product corresponding to the carbodiimide is removed by suction filtration. The filtrate solution is then washed and dried, and the reaction solvent is then evaporated to recover the crude reaction product. The crude product is then purified, for example, by flash chromatography.

Carbodiimides suitable for use with the present invention include dicyclohexylcarbo-diimide (DCC), 1-ethyl-3-(3-dimethylaminopropyl)carbodiimide, 1-alkyl-3-(3-dimethylaminopropyl)carbodiimide(alkyl=isopropyl, cyclochexyl),1-cyclohexyl-3-(2-morpholinyl(4-ethyl)) carbodiimide, 1-cyclohexyl-3-(4-diethylaminocyclohexyl) carbodiimide, 1-cyclohexyl-3-(diethylaminoethyl) carbodiimide, 1,3-di-(4-diethylaminocyclohexyl) carbodiimide, 1-alkyl-3-(3-morpholinyl-(4-propyl)) carbodiimide (alkyl=methyl, ethyl), 1-benzyl-3-(3-dimethylamino-(N)-propyl)carbodiimide, and 1-ethyl-3-(4-azonia-4,4-dimethylpentyl)carbodiimide. In each case, the carbodiimide is used as the free base or a salt (HCl, methiodide, metho-p-toluenesulfonate, and the like). The preferred carbodiimide is DCC.

Carbodiimide-mediated coupling reactions are also used to create an amino acid or peptide linkage between the core polyol hydroxyl groups or core polyamine amino groups and the acylated dicarboxylic acids. The coupling reaction is first performed between the core polyol or polyamine and the amino acid or peptide, after which the amino acid or peptide-branched polyol or polyamine is then reacted with the acylated dicarboxylic acid in another carbodiimide-mediated coupling reaction.

The poly(alkylene oxide) chains are then attached by reacting the substituted core polyol or polyamine with an activated poly(alkylene oxide) in another carbodiimide-mediated coupling reaction. To attach the poly(alkylene oxide) chains by way of an amide linkage, poly(alkylene oxide) amines are employed. For an ester linkage, a poly(alkylene oxide) is employed. For an anhydride linkage, a poly(alkylene oxide) carboxylic acid is employed. Other linkages represented by Q in the above formulas that are suitable for use with the present invention are well known to those skilled in the pegylation art and require no further description.

A reaction mixture of the substituted core polyol and the activated poly(alkylene oxide) in a common solvent such as methylene chloride is formed. A quantity of a solution providing a molar equivalent of carbodiimide and DMAP for each substituted hydroxyl group of the core polyol, dissolved in a common solvent such as methylene chloride, is then added to the reaction mixture. The reaction mixture is maintained at room temperature with stirring for at least 12 hours, after which it is evaporated to dryness, followed by purification, for example by recrystallization, followed by flash chromatography.

The polymers of the present invention have a number average molecular weight between about 1,000 and about 100,000 daltons, measured by Gel Permeation Chromatography relative to polystyrene standards. Molecular weights between about 2,500 and about 25,000 daltons are preferred.

The resulting polymers may be used for essentially any application in which conventional micelles are employed. Examples include drug solubilization, fragrance encapsulation, passive targeting for drug delivery, waste water treatment, enhanced capillary electrophoresis activation, and induction of protein crystallization. Alkali metal cations may also be encapsulated by the polymer to form solvent-free polymer-salt complex solid electrolytes.

The polymers of the present invention are particularly useful in solubilizing hydrophobic molecules, particularly hydrophobic molecules with biological or pharmaceutical activity for drug delivery.

According to one embodiment of the present invention, hydrophobic molecules are encapsulated by dissolving the hydrophobic molecules and the polymer in a common solvent, such as methylene chloride. The solvent is then removed, for example, by rotoevaporation. The resulting solid is then washed thoroughly with a non-polar solvent such as hexane, to remove any residual non-encapsulated hydrophobic materials. The washed solid is then thoroughly dried, preferably under vacuum, to completely remove any adsorbed solvent, and to obtain the essentially pure polymer-encapsulated hydrophobic material.

According to an alternative embodiment, the polymer of the present invention is dissolved in water, and an excess quantity of the hydrophobic material is added to the aqueous solution, with stirring. After allowing the hydrophobic material sufficient contact with the aqueous polymer solution, the excess hydrophobic material is permitted to separate from the aqueous solution, after which it is removed. The polymer-encapsulated material may then be kept in this aqueous solution, or the aqueous solution may be concentrated, or the polymer encapsulate may be recovered in dry form by evaporating the water.

When the water is evaporated, the dried polymer may be subjected to non-polar solvent rinsing to remove any residual hydrophobic material and further evaporation to remove any residual adsorbed non-polar solvent.

The present invention contemplates the use of polymer-encapsulated hydrophobic molecules at concentrations as high as 1 M and greater, up to $10^6$ M. At the same time, another advantage of the present invention is the thermodynamic stability of the polymers, which permit the formation of low concentration stable aqueous solutions of the polymer encapsulates, far below the CMC's of conventional surfactants. Stable aqueous solutions as low as $10^{-10}$ M have been obtained, although, at present, concentrations of $10^{-8}$ and greater are expected to have the greatest commercial utility. The polymers of the present invention are believed to form stable aqueous encapsulate solutions below the presently available limits of detection, i.e., below $10^{-10}$ M.

Pharmaceutical dosage forms of polymer-encapsulated hydrophobic molecules having biological or pharmaceutical activity may be formulated using physiologically acceptable carriers, excipients, stabilizers and the like, and may be provided in sustained release or timed release formulation. Acceptable carriers, excipients and diluents for therapeutic use are well known in the pharmaceutical field, and are described, for example, in *Remington's Pharmaceutical Science* (A. R. Gennaro Edit., Mack Publishing Co., 1985). Such materials are non-toxic to the recipients at the dosages and concentrations employed, and include buffers such as phosphate, citrate, acetate and other organic acid salts, antioxidants such as ascorbic acid, low molecular weight (less than about 10 residues) peptides such as polyarginine, proteins, such as serum albumin, gelatin and immunoglobulins, hydrophillic polymers such as poly (vinylpyrrolidinone), amino acids such as glycine, glutamic acid, aspartic acid and arginine, monosaccharides, disaccharides, and other carbohydrates, including cellulose and its derivatives, glucose, mannose and dextrines, chelating agents such as EDTA, sugar alcohols such as mannitol and sorbitol, and conventional cationic and nonionic surfactants such as TWEEN, PULRONICS, and PEG.

Dosage formulations to be used for therapeutic administration must be sterile. Sterility is readily accomplished by filtration through sterile membranes, or by other conventional methods such as irradiation or treatment with gases or heat. The pH of the dosage formulations of this invention typically will be between 3 and 11, and more preferably from 5 to 9.

Patients in need of treatment (typically mammalian) using the dosage formulations of this invention can be administered dosages that will provide optimal efficacy. The dose and method of administration will vary from subject to subject and be dependent upon such factors as the type of mammal being treated, its sex, weight, diet, concurrent medication, overall clinical condition, the particular hydrophobic compounds employed, the specific use for which these compounds are employed, and other factors which those skilled in the medical arts will recognize.

Therapeutically effective dosages may be determined by either in vitro or in vivo methods. For each particular dosage form of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each hydrophobic compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

A typical dosage might range from about 0.001 mg to about 1,000 mg of hydrophobic material, per kg of patient weight. Preferred dosages range from about 0.01 mg/kg to about 100 mg/kg, and more preferably from about 0.10 mg/kg to about 20 mg/kg. Advantageously, the dosage forms of this invention may administered several times daily, and other dosage regimens may also be useful.

The dosage formulations of this invention may be prepared for storage under conditions suitable for the preservation of the biological or pharmaceutical activity of the hydrophobic material, as well as for maintaining the integrity of the polymer, and are typically suitable for storage in ambient or refrigerated temperatures. The polymer encapsulates of the present invention may be formulated for administration orally, subcutaneously, intramuscularly, intravenously, colonically, rectally, nasally or intraperitonially, employing a variety of dosage forms such as solutions, tablets, capsules, gelcaps, suppositories, implanted pellets or small cylinders, aerosols and topical formulations such as lotions, ointments, drops and dermal patches. The dosage formulations of this invention are suitable for applications where localized drug delivery is desired, as well as in situations where a systemic delivery is desired.

The dosage formulations of this invention may desirably further incorporate agents to facilitate the systemic delivery of the hydrophobic material having biological or pharmaceutical activity to the desired target. The hydrophobic materials to be delivered may, in this fashion, be incorporated with antibodies, antibody fragments, growth factors, hormones, or other targeting moieties, to which the drug molecules are coupled. The present invention also contemplates the use of peptide linkages between the core polyol and the acylated dicarboxylic acids that are selected for cleavage by proteolytic enzymes, resulting in degradation of the polymer and release of the encapsulated hydrophobic material. The release of the hydrophobic material may thus be targeted by selecting a peptide sequence corresponding to a proteolytic enzyme unique to the target site, or by co-administering a proteolytic enzyme corresponding to the peptide sequence at the target site for the hydrophobic material.

However, one advantage of the polymers of the present invention is that polymer degradation is not a prerequisite for release of the hydrophobic material.

Practically any hydrophobic therapeutic agent otherwise suitable for the practice of this invention may be employed for a variety of therapeutic applications. The polymers of the present invention may also be used as thickening agents, lubricants, detergents surfactants, plasticizers and anti-fouling agents. The polymers may be used as an emulsifying, dispersing or stabilizing agent for dyes, cosmetics, pigment and pharmaceutical products. The polymers are particularly useful as an emulsifying, dispersing or stabilizing agent in the dyeing of textiles and for encapsulating dyes for cosmetics. The polymers are useful as lubricants and encapsulants for cosmetics, textiles, leathers and perfumes, and are particularly useful as a thickening agent for paints. The polymers may also be employed as an emulsifying, dispersing or stabilizing agent for components of photographic compositions and developers.

Thus, in addition to biologically or pharmaceutically active hydrophobic molecules, other hydrophobic molecules that may be encapsulated by the polymers of the present invention include insecticides, pesticides, herbicides, antiseptics, food additives, fragrances, dyes, diagnostic aids, and the like. Examples of hydrophobic molecules that may be encapsulated by the polymers of the present invention include, but are not limited to:

abietic acid, aceglatone, acenaphthene, acenocoumarol, acetohexamide, acetomeroctol, acetoxolone, acetyldigitoxins, acetylene dibromide, acetylene dichloride, acetylsalicylic acid, alantolactone, aldrin, alexitol sodium, allethrin, allylestrenol, allyl sulfide, alprazolam, aluminum bis(acetylsalicylate), ambucetamide, aminochlothenoxazin, aminoglutethimide, amyl chloride, androstenediol, anethole trithone, anilazine, anthralin, Antimycin A, aplasmomycin, arsenoacetic acid, asiaticoside, astemizole, aurodox, aurothioglycanide, 8-azaguanine, azobenzene;

baicalein, Balsam Peru, Balsam Tolu, barban, baxtrobin, bendazac, bendazol, bendroflumethiazide, benomyl, benzathine, benzestrol, benzodepa, benzoxiquinone, benzphetamine, benzthiazide, benzyl benzoate, benzyl cinnamate, bibrocathol, bifenox, binapacryl, bioresmethrin, bisabolol, bisacodyl, bis(chlorophenoxy)methane, bismuth iodosubgallate, bismuth subgallate, bismuth tannate, Bisphenol A, bithionol, bornyl, bromoisovalerate, bornyl chloride, bornyl isovalerate, bornyl salicylate, brodifacoum, bromethalin, broxyquinoline, bufexamac, butamirate, butethal, buthiobate, butlated hydroxyanisole, butylated hydroxytoluene;

calcium iodostearate, calcium saccharate, calcium stearate, capobenic acid, captan, carbamazepine, carbocloral, carbophenothin, carboquone, carotene, carvacrol, cephaeline, cephalin, chaulmoogric acid, chenodiol, chitin, chlordane, chlorfenac, chlorfenethol, chlorothalonil, chlorotrianisene, chlorprothixene, chlorquinaldol, chromonar, cilostazol, cinchonidine, citral, clinofibrate, clofazimine, clofibrate, cloflucarban, clonitrate, clopidol, clorindione, cloxazolam, coroxon, corticosterone, coumachlor, coumaphos, coumithoate cresyl acetate, crimidine, crufomate, cuprobam, cyamemazine, cyclandelate, cyclarbamate cymarin, cypernethril;

dapsone, defosfamide, deltamethrin, deoxycorticocosterone acetate, desoximetasone, dextromoramide, diacetazoto, dialifor, diathymosulfone, decapthon, dichlofluani, dichlorophen, dichlorphenamide, dicofol, dicryl, dicumarol, dienestrol, diethylstilbestrol, difenamizole, dihydrocodeinone enol acetate, dihydroergotamine, dihydromorphine, dihydrotachysterol, dimestrol, dimethisterone, dioxathion, diphenane, N-(1,2-diphenylethyl)nicotinamide, dipyrocetyl, disulfamide, dithianone, doxenitoin, drazoxolon, durapatite, edifenphos, emodin, enfenamic acid, erbon, ergocorninine, erythrityl tetranitrate, erythromycin stearate, estriol, ethaverine, ethisterone, ethyl biscoumacetate, ethylhydrocupreine, ethyl menthane carboxarnide, eugenol, euprocin, exalamide;

febarbamate, fenalamide, fenbendazole, fenipentol, fenitrothion, fenofibrate, fenquizone, fenthion, feprazone, flilpin, filixic acid, floctafenine, fluanisone, flumequine, fluocortin butyl, fluoxymesterone, flurothyl, flutazolamn, fumagillin, 5-furfuryl-5-isopropylbarbituric acid, fusafungine, glafenine, glucagon, glutethimide, glybuthiazole, griseofulvin, guaiacol carbonate, guaiacol phosphate, halcinonide, hematoprphyrin, hexachlorophene, hexestrol, hexetidine, hexobarbital, hydrochlorothiazide, hydrocodone, ibuproxam, idebenone, indomethacin, inositol niacinate, iobenzamic acid, iocetamic acid, iodipamide, iomeglamic acid, ipodate, isometheptene, isonoxin, 2-isovalerylindane-1,3-dione;

josamycin, 11-ketoprogesterone, laurocapram, 3-O-lauroylpyridoxol diacetate, lidocaine, lindane, linolenic acid, liothyronine, lucensomycin, mancozeb, mandelic acid, isoamyl ester, mazindol, mebendazole, mebhydroline, mebiquine, melarsoprol, melphalan, menadione, menthyl valerate, mephenoxalone, mephentermine, mephenytoin, meprylcaine, mestanolone, mestranol, mesulfen, metergoline, methallatal, methandriol, methaqualone, 3-methylcholanthrene, methylphenidate, 17-methyltestosterone, metipranolol, minaprine, myoral, naftalofos, naftopidil, naphthalene, 2-naphthyl lactate, 2-(2-naphthyloxy)ethanol, naphthyl salicylate, naproxen, nealbarbital, nemadectin, niclosamide, nicoclonate, nicomorphine, nifuroquine, nifuroxazide, nitracrine, nitromersol, nogalamycin, nordazepamn, norethandrolone, norgestrienone;

octaverine, oleandrin, oleic acid, oxazepam, oxazolam, oxeladin, oxwthazaine, oxycodone, oxymesterone, oxyphenistan acetate, paraherquamide, parathion, pemoline, pentaerythritol tetranitrate, pentylphenol, perphenazine, phencarbamide, pheniramine, 2-phenyl-6-chlorophenol, phentlmethylbarbituric acid, phenytoin, phosalone, phthalylsulfathiazole, phylloquinone, picadex, pifarnine, piketopfen, piprozolin, pirozadil, plafibride, plaunotol, polaprezinc, polythiazide, probenecid, progesterone, promegestone, propanidid, propargite, propham, proquazone, protionamide, pyrimethamine, pyrimithate, pyrvinium pamoate;

quercetin, quinbolone, quizalofo-ethyl, rafoxanide, rescinnamine, rociverine, ronnel salen, scarlet red, siccanin, simazine, simetride, sobuzoxane, solan, spironolactone, squalene, stanolone, sucralfate, sulfabenz, sulfaguanole, sulfasalazine, sulfoxide, sulpiride, suxibuzone, talbutal, terguide, testosterone, tetrabromocresol, tetrandrine, thiacetazone, thiocolchicine, thioctic acid, thioquinox, thioridazine, thiram, thymyl N-isoamylcarbamate, tioxidazole, tioxolone, tocopherol, tolciclate, tolnaftate, triclosan, triflusal, triparanol;

ursolic acid, valinomycin, veraparnil, vinblastine, vitamin A, vitamin D, vitamin E, xenbucin, xylazine, zaltoprofen, and zearalenone.

A particular class of hydrophobic molecules having biological activity that are suitable for use with the present invention are inter-cellular regulators and mediators such as interferons, growth factors, hormones, and the like. The polymers of the present invention are contemplated to be particularly effective for the efficient administration of interferons, which have proven to be problematic because of interferon's water-insolubility. As noted above, the topical dosage forms of the present invention exhibit an unexpectedly accelerated rate of transdermal delivery attributable to the encapsulation of the hydrophobic material by the polymers of the present invention. Thus, the polymer-encapsulated hydrophobic material having biological or pharmaceutical activity may be prepared as topical dosage forms such as lotions, gels, salves, creams, balms, ointments and the like. These compositions may be in the form of aqueous solutions, or in the form of oil-in-water or water-in-oil emulsions. The formulations are essentially conventional, containing well-known additives, and are prepared using art-recognized techniques.

Topical dosage forms may also be prepared by incorporating the polymer encapsulate into the reservoir of a transdermal drug delivery device. Transdermal administration systems, or "patches", are well-known in the art. Occlusive transdermal patches for the administration of an active agent to the skin or mucosa are described in U.S. Pat. Nos. 4,573,966; 4,597,961 and 4,839,164, the disclosures of which are incorporated herein by reference. Essentially any device capable of delivering an active agent transdermally may be employed to transdermally deliver the polymer encapsulate of the present invention.

As noted above, the polymer encapsulates are rapidly delivered, providing a "burst effect" dosage of the polymer encapsulate. Thus, the reservoir of the transdermal delivery device may also incorporate the biologically or pharmaceutically active hydrophobic molecule in a non-encapsulated form to sustain delivery beyond the initial "burst." Alternatively, the transdermal patch may be intended only for a rapid dose delivery, in which case the reservoir would only contain the polymer encapsulate as the active agent.

The following non-limiting examples set forth hereinbelow illustrate certain aspects of the invention. All parts and percentages are by weight unless otherwise noted and all temperatures are in degrees Celsius. All PEG's were obtained from Shearwater Polymers (Birmingham, Ala.) and used without further purification. All other chemicals were obtained from Aldrich (Milwaukee, Wis.) and used without further purification. Analytical grade solvents were used for all the reactions. Methylene chloride, tetrahydrofuran (THF), triethylamine (TEA) and dimethylsulfoxide (DMSO) were distilled. Nuclear magnetic resonance spectroscopy ($^1$H NMR, $^{13}$C NMR), infrared spectroscopy (IR), mass spectrometry (MS), gel permeation chromatography (GPC) and elemental analysis were used for physicochemical characterization. For differential scanning calorimetry (DSC) measurements, samples were heated under dry nitrogen gas. Data were collected at heating and cooling rates of 10° C./min. with a two cycle minimum. For thermogravimetric analysis (TGA), samples were also heated under dry nitrogen gas. Data were collected at a heating rate of 20° C/min. Molecular weights were determined by GPC relative to narrow molecular weight polystyrene standards.

EXAMPLES

Examples 1–3
Acylation of Mucic Acid

Example 1
Mucic Acid Propyl Ester

To a neat mixture of mucic acid (4.2 g, 20 mmol) and propionyl chloride (18 ml, 200 mmnol) was added $ZnCl_2$ (0.28 g, 2.0 mmol). The reaction mixture was heated at reflux temperature for three hours. After cooling, diethyl ether (20 ml) was added to the reaction mixture and the solution poured onto ice chips (approximately 100 g) with stirring. Additional diethyl ether (80 ml) was added to the mixture and stirring continued for 30 minutes more. The ether portion was separated, washed with water to a neutral pH, dried over anhydrous $Na_2SO_4$ and evaporated to dryness. The crude product was purified by recrystallization from a cosolvent system of diethyl ether and methylene chloride, collected by vacuum filtration, washed by ice cold methylene chloride and dried at 105° C. (12 hours) to constant weight. A white solid having a $T_m$ of 196° C. was obtained at a 56% yield.

Example 2
Mucic Acid Hexyl Ester

Mucic acid hexyl ester was prepared as in Example 1, substituting caproyl chloride for propionyl chloride. A white solid having a $T_m$ of 171° C. was obtained at a yield of 68%.

Example 3
Mucic Acid Lauryl Ester

Mucic acid lauryl ester was prepared as in Example 1, substituting lauryl chloride for propionyl chloride. A white solid having a $T_m$ of 145° C. was obtained at a yield of 65%.

Examples 4–6
Preparation of Polymer Core

Example 4
Propyl Ester

The mucic acid propyl ester of Example 1 (6.0 mmol) and 1,1,1-tris(4'-hydroxyphenyl)ethane (0.51 g, 1.7 mmol) were dissolved in anhydrous ethyl ether (150 ml). To the reaction mixture, a solution of DCC (1.2 g, 6.0 mmol) and DMAP (0.74 g, 6.0 mmol) in 25 ml methylene chloride was added dropwise. After 15 minutes, the DCC side-product (dicyclohexylurea) was removed by suction filtration. The filtrate was washed with 20 ml portions of 0.1 N HCL (2x) and brine (4x), dried over anhydrous $Na_2SO_4$, and evaporated to dryness. The crude product was purified by flash chromatography using ethyl ether: methanol: acetic acid (90:5:5) as eluent. A white solid having a $T_m$ of 158° C. was obtained at 58% yield.

Example 5
Hexyl Ester

The hexyl ester core molecule was prepare according to the method of Example 4, substituting the mucic acid hexyl ester of Example 2 for the mucic acid propyl ester. A white solid having a $T_m$ of 147° C. was obtained at 36% yield.

Example 6
Lauryl Ester

The lauryl ester core molecule was prepared according to the method of Example 4, substituting the mucic acid lauryl ester of Example 3 for the mucic acid propyl ester. A white solid having a $T_m$ of 136° C. was obtained at yield of 33%.

Examples 7–11
Preparation of Final Polymers

Example 7
Mucic Acid Hexyl Ester Core Polymer With Triethylene Glycol (TEG) Branches To a mixture of the core molecule of Example 5 (0.106 mmol) and methoxy-terminated triethylene glycol amine (0.351 mmol) in 20 ml of methylene chloride at room temperature, DCC (0.351 mmol) and DMAP (0.351 mmol) in 2 ml methylene chloride was added dropwise. After three days, the reaction mixture was evaporated to dryness, the residue dissolved into 20 ml methanol, and the crude product precipitated from 400 ml petroleum ether at room temperature. The crude product was first purified by flash chromatography using ethyl ether: methanol: acetic acid (90:5:5) as eluent, then further purified by repetitive precipitation using methylene chloride as solvent and diethyl ether/petroleum ether as non-solvent. The ratio between methylene chloride and ethers was progressively changed. A white solvent was obtained having a $T_m$ of 31° C., a $T_d$ of 220° C. and $M_W$ of 2,400 daltons at a yield of 15%.

Example 8
Mucic Acid Hexyl Ester Core Polymer With PEG 2000 Branches

A mucic acid hexyl ester core polymer with PEG 2000 branches was prepared according to the method of Example 7, substituting methoxy-terminated poly(ethylene glycol) amine ($H_2N$-m-PEG 2000, $M_W$=2000) for the methoxy-terminated triethylene glycol amine of Example 7. A white solid was obtained having a $T_m$ of 54° C. and a $M_W$ of 9,400 daltons at a yield of 25%.

Example 9
Mucic Acid Hexyl Ester Core Polymer With PEG 5000 Branches

A mucic acid hexyl ester core polymer with PEG 5000 branches was prepared according to the method of Example 7, substituting methoxy-terminated poly(ethylene glycol) amine ($H_2N$-PEG 5000, $M_W$=5000) for the methoxy-terminated triethylene glycol amine of Example 7. A white solid having a $T_m$ of 61° C. and a $M_W$ of 17,800 daltons was obtained at 17% yield.

Example 10
Mucic Acid Propyl Ester Core Polymer With PEG 5000 Branches

Mucic acid propyl ester core polymer with PEG 5000 branches was prepared according to the method of Example 9, substituting the mucic acid propyl ester core polymer of Example 4 for the mucic acid hexyl ester core polymer. A white solid was obtained having a $T_m$ of 62° C. and a $M_W$ of 17,000 daltons at 30% yield.

Example 11
Mucic Acid Lauryl Ester Core Polymer With PEG 5000 Branches

Mucic acid lauryl ester core polymer with PEG 5000 branches was prepared according to the method of Example 9, substituting the mucic acid lauryl ester core polymer of Example 6 for the mucic acid hexyl ester core polymer. A white solid was obtained having a $T_m$ of 60° C. and a $M_W$ of 19,100 daltons at a yield of 45%.

For the polymers of Examples 8–11, TGA showed two stages of decomposition. The first stage corresponded to cleavage of the core structures from the ethylene oxide chains (about 200° C.) with the appropriate weight loss, and the second stage corresponded to decomposition of the ethylene oxide chain.

Example 12
Encapsulation Studies

Lidocaine (50 mg) and the polymer of Example 9 (50 mg) were dissolved in 2.0 ml methylene chloride. The solution was evaporated to dryness and the solid residue extensively washed with hexane until lidocaine was no longer detected in the washings. The solid was dried under vacuum at 25° C. for about 2 hours. A portion (5.0 mg) of this solid was dissolved into methanol (1.0 ml) to release the entrapped lidocaine, and the lidocaine concentration was quantified by high pressure liquid chromatography (HPLC) according to a calibration curve generated from a series of standard solutions ranging from 0.005 to 0.5 mg/ml lidocaine. The linearity of the curve indicated a direct, proportional relationship between absorbance and lidocaine concentration. Using the equation of the lidocaine calibration curve, the amount of lidocaine entrapped in the unimolecular micelle core was determined. PEG with a molecular weight of 5,000 daltons was used as the HPLC control.

Encapsulation number was defined as the amount of molecules that can be entrapped within the polymeric micelles. The values for the polymers of Example 9, 10 and 11 were 1.0, 0.7 and 1.6 weight %, respectively. The encapsulation number increased as the hydrophobicity of the polymer interior increased.

The PEG arms of the polymers of the present invention thus form a hydrophilic shell that solubilizes the polymer in water, while the core forms a hydrophobic microenvironment that encapsulates small hydrophobic molecules. Unlike conventional micelles, however, the polymeric micelles of the present invention are thermodynamically stable because of the covalent linkages between the polymer arms. The ability to encapsulate small molecules, the enhanced solubility and the lack of aggregation characterize the usefulness of these polymers as drug delivery systems. Candidate drugs, of which there are many, have aromatic or heteroaromatic moieties and carbonyl functionalities (e.g., amides and carboxylates). The biocompatibility and biodegradability of these polymers further characterize their utility for drug delivery. The excellent water-solubility of these polymers makes intravenous injection and oral administration of hydrophobic drug molecules possible. For controlled release applications, the small size of these polymers, along with their enhanced thermodynamic stability, further characterizes their utility.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A polymer having a structure selected from the group consisting of:

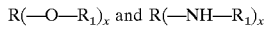

wherein $R(-O-)_x$ is obtained from a polyol and $R(-NH-)_x$ is obtained from a polyamine, with x being between 2 and 10, inclusive, and each $R_1$ independently has the structure:

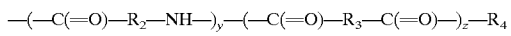

wherein
—C(=O)—$R_2$—NH— is obtained from a divalent amino acid with $R_2$ being a covalent bond or having from 1–8 carbon atoms, and y and z are between 0 and 10 inclusive, provided y and z are not both 0;

—C(=O)—$R_3$—C(=O)— is obtained from a divalent dicarboxylic acid in which $R_3$ is an alkylene or cycloalkylene group containing from 1 to 15 carbon atoms, substituted with a total of from 1 to about 10 hydroxyl groups, with at least a portion of the hydroxyl groups being acylated with from 3 to about 24 carbon atom carboxylic acids;

$R_4$ is a poly(alkylene oxide) having the structure:

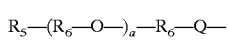

$R_5$ is selected from the group consisting of 1 to 40 carbon atom alkyl groups, —OH, —OR$_7$, —NH$_2$, —NHR$_7$, —NHR$_7$R$_8$, —CH$_2$—OH, —CH$_2$—OR$_7$, —CH$_2$—O—CH$_2$—R$_7$, CH$_2$—NH$_2$, —CH$_2$—NHR$_7$ and CH$_2$—NR$_7$R$_8$;

$R_6$, $R_7$, and $R_8$ are independently selected from the group consisting of 2 to 40 carbon atom, straight-chain or branched alkylene groups, Q is a divalent linkage moiety; and a is between 2 and 110, inclusive;

provided that when y is 0 and R is a 1,1,1-tris (hydroxyphenyl)ethane moiety, the divalent dicarboxylic acid moiety is not an acylated mucic acid moiety.

2. The polymer of claim 1, wherein R(—O—)$_x$ is obtained from an aliphatic polyol having from 1 to 10 carbon atoms.

3. The polymer of claim 1, wherein R(—O—)$_x$ is obtained from a cycloaliphatic polyol.

4. The polymer of claim 3, wherein the cycloaliphatic polyol is a sugar.

5. The polymer of claim 1, wherein R(—O—)$_x$ is obtained from an aromatic polyol.

6. The polymer of claim 5, wherein the aromatic polyol is 1,1,1-tris(4'-hydroxyphenyl)ethane, (1,3-adamantanediyl) diphenol, 2,6-bis(hydroxyalkyl)cresol, 2,2'-alkylene-bis(6-tert-butyl-4-alkylphenol), 2,2'-alkylene-bis(t-butylphenol), catechol, an alkylcatechol, pyrogallol, fluoroglycinol, 1,2,4-benzenetriol, resorcinol, an alkylresorcinol, a dialkylresorcinol, orcinol monohydrate, olivetol, hydroquinone, an alkylhydroquinone, 1,1-bi-2-naphthol, a phenyl hydroquinone, a dihydroxynaphthalene, 4,4'-(9-fluorenylidene)-diphenol, anthrarobin, dithranol, bis (hydroxyphenyl) methane, a biphenol, a dialkylstilbeterol, a bis(hydroxyphenyl) alkane, or bisphenol-A.

7. The polymer of claim 1, wherein R(—O—)$_x$ is obtained from a hydroxylated crown ether, a cyclodextrin, or a dextrin.

8. The polymer of claim 1 which has a number average molecular weight between about 1,000 and about 100,000 daltons.

9. The polymer of claim 1 which has a number average molecular weight between about 2,500 and about 25,000 daltons.

10. The polymer of claim 1, wherein x is 3 or 4.

11. The polymer of claim 10, having the structure R(—NH—R$_1$)$_x$, wherein R(—NH— is obtained from a polyamine.

12. The polymer of claim 10, having the structure R(—O—R$_1$)$_x$, wherein R(—O—)$_x$ is obtained from a polyol.

13. The polymer of claim 12, wherein said polyol moiety is an aromatic polyol moiety.

14. The polymer of claim 13, wherein said polyol moiety is a 1,1,1-tris(hydroxyphenyl)ethane moiety.

15. The polymer of claim 1, wherein every hydroxyl group of said divalent dicarboxylic acid moiety is acylated with a 6 to 24 carbon atom carboxylic acid group.

16. The polymer of claim 15, wherein y is 0.

17. The polymer of claim 15, wherein said divalent dicarboxylic acid moiety is a mucic acid moiety.

18. The polymer of claim 12, wherein said polyol moiety is an aliphatic or cycloaliphatic polyol moiety.

19. The polymer of claim 14, wherein said polyol moiety is a cyclic crown ether or cyclodextrin moiety.

20. The polymer of claim 1, wherein said poly(alkylene oxide) is a methoxy-terminated poly(ethylene glycol) and Q is —NH—.

21. The polymer of claim 1, wherein Q is —O—, or forms anhydride linkage.

* * * * *

UNITED STATES PATENT AND TRADEMARK OFFICE
CERTIFICATE OF CORRECTION

PATENT NO. : 6,365,146 B1
DATED : April 2, 2002
INVENTOR(S) : Kathryn E. Uhrich

It is certified that error appears in the above-identified patent and that said Letters Patent is hereby corrected as shown below:

Title page,
Item [56], OTHER PUBLICATIONS, delete "J.M.Harris" and insert
-- J.M. Harris --, therefor.

Item [57], ABSTRACT, delete:

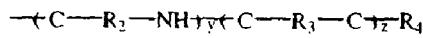

and insert:

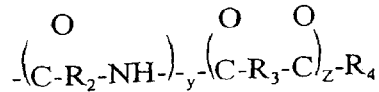

Insert -- is -- before "a divalent"; and delete "–OH–," and insert -- –OH, --, therefor; and delete "–NH–," and insert -- –NH$_2$, --, therefor.

Column 17,
Line 4, delete "CH$_2$–NH$_2$," and insert -- –CH$_2$–NH$_2,$ --, therefor.
Lines 4-5, delete "CH$_2$–NR$_7$R$_8$;" and insert -- –CH$_2$–NR$_7$R$_8$; --, therefor.

UNITED STATES PATENT AND TRADEMARK OFFICE
CERTIFICATE OF CORRECTION

PATENT NO. : 6,365,146 B1
DATED : April 2, 2002
INVENTOR(S) : Kathryn E. Uhrich

It is certified that error appears in the above-identified patent and that said Letters Patent is hereby corrected as shown below:

Column 18,
Line 10, delete "R(–NH–" and insert -- R(–NH–)$_x$ --, therefor.
Line 28, delete "claim 14" and insert -- claim 12 --, therefor.
Line 35, insert -- an -- between "forms" and "anhydride".

Signed and Sealed this

Fifteenth Day of April, 2003

JAMES E. ROGAN
*Director of the United States Patent and Trademark Office*